United States Patent [19]

Santilli et al.

[11] Patent Number: 4,496,786

[45] Date of Patent: Jan. 29, 1985

[54] SELECTIVE CONVERSION OF METHANOL TO LOW MOLECULAR WEIGHT OLEFINS OVER HIGH SILICA SSZ-13 ZEOLITE

[75] Inventors: Donald S. Santilli, Novato; Stacey I. Zones, San Francisco, both of Calif.

[73] Assignee: Chevron Research Company, San Francisco, Calif.

[21] Appl. No.: 538,035

[22] Filed: Sep. 30, 1983

[51] Int. Cl.³ .............................................. C07C 1/00
[52] U.S. Cl. ................................................... 585/640
[58] Field of Search ....................................... 585/640

[56] References Cited

U.S. PATENT DOCUMENTS

| | | | |
|---|---|---|---|
| 4,062,905 | 12/1977 | Chang et al. | 585/640 |
| 4,156,698 | 5/1979 | Dwyer et al. | 585/408 |
| 4,229,608 | 10/1980 | Chen et al. | 585/640 |
| 4,372,878 | 2/1983 | Wunder et al. | 502/60 |

*Primary Examiner*—Curtis R. Davis
*Attorney, Agent, or Firm*—J. A. Buchanan, Jr.; S. R. La Paglia

[57] ABSTRACT

A process for the conversion of methanol to olefins by contacting an methanol-containing feedstock with an SSZ-13 under methanol conversion conditions.

3 Claims, No Drawings

4,496,786

SELECTIVE CONVERSION OF METHANOL TO LOW MOLECULAR WEIGHT OLEFINS OVER HIGH SILICA SSZ-13 ZEOLITE

TECHNICAL FIELD

Natural and synthetic aluminosilicates are important and useful compositions. Many of these alumino-silicates are porous and have definite, distinct crystal structures as determined by X-ray diffraction. Within the crystals are a large number of cavities and pores whose dimensions and shapes vary from zeolite to zeolite. Variations in pore dimensions and shapes cause variations in the adsorptive and catalytic properties of the zeolites. Only molecules of certain dimensions and shapes are able to fit into the pores of a particular zeolite while other molecules of larger dimensions or different shapes are unable to penetrate the zeolite crystals.

Because of their unique molecular sieving characteristics, as well as their potentially acidic nature, zeolites are especially useful in hydrocarbon processing as adsorbents, and, as catalysts, for cracking, reforming, and other hydrocarbon conversion reactions. Although many different crystalline aluminosilicates have been prepared and tested, the search for new zeolites which can be used in hydrocarbon and chemical processing continues.

In copending U.S. patent application Ser. No. 519,954, filed Aug. 3, 1983, there is disclosed a novel family of crystalline aluminosilicate zeolites, hereinafter designated "Zeolite SSZ-13" or simply "SSZ-13", and methods for their preparation and use. The disclosure of Ser. No. 519,954 is herein incorporated by specific reference.

In many catalytic processes where there is no hydrogen and a corresponding hydrogenation metal present, coke formation is a potentially deactivating process. One way to reduce coke formation is to increase the $SiO_2/Al_2O_3$ ratio of a material (particularly a zeolite) by (1) increasing the ratio via synthetic means or, (2) by treatments intended to remove $Al_2O_3$ from the structure.

SSZ-13 is a small-pore zeolite which does not admit even singly-branched hydrocarbons. However, because of the pore and cavity structure of the zeolite, and because under some synthetic routes the $SiO_2/Al_2O_3$ is less than or equal to about 12, coke formation and catalyst deactivation during hydrocarbon cracking may be very fast. Coke formation can be observed to occur rapidly when methanol is dehydrated to higher hydrocarbons over $H^+$-SSZ-13.

The conversion of methanol to low molecular weight olefins ($C_2$ to $C_4$) is a desirable process. We believed that a small-pore zeolite would be the ideal catalyst as it would be more difficult to form larger hydrocarbons, especially aromatics, which can subsequently produce alkanes from olefins via hydrogen transfer reactions. Initial experiments using erionite and then SSZ-13 ($SiO_2/Al_2O_3 < 12$) as zeolite catalysts produced about 70% olefins ($C_2$ to $C_4$), 30% alkanes, and no aromatics. Coke formation was sufficiently rapid that the catalysts deactivated substantially within one hour on stream. Furthermore, coke formation (releasing hydrogen) was so rapid that enough hydrogen was transferred to the initial olefin products to produce the 30% (wt) alkanes observed.

SUMMARY OF THE INVENTION

The conversion of methanol to olefins occurs advantageously by contacting a methanol feedstock with SSZ-13 zeolite having an $SiO_2/Al_2O_3$ weight ratio greater than about 20 under methanol conversion conditions. Preferably, the $SiO_2/Al_2O_3$ weight ratio of SSZ-13 is greater than 30 and most preferably it is greater than 40.

DETAILED DESCRIPTION OF PREFERRED EMBODIMENTS

In the process of the present invention a methanol feedstock comprises any liquid or gaseous feedstock containing methanol.

In the process of the present invention methanol conversion conditions comprise a temperature in the range of from about 550° F. to about 850° F., preferably from about 700° F. to about 800° F., at a space velocity of grams of methanol per gram of SSZ-13 per hour of from about 0.1 g/g/hr to about 10 g/g/hr, preferably from about 0.5 g/g/hr to about 2 g/g/hr, and at a pressure of about 1 atmosphere or higher.

In general, SSZ-13 is a zeolite having a mole ratio of an oxide selected from silicon oxide, germanium oxide, and mixtures thereof to an oxide selected from aluminum oxide, gallium oxide, and mixtures thereof greater than about 5:1 and having the X-ray diffraction lines of Table 1. The zeolite further has a composition, as synthesized and in the anhydrous state, in terms of mole ratios of oxides as follows: (0.5 to 1.4)$R_2O$:(0 to 0.50)$M_2O$:$W_2O_3$:(greater than 5)$YO_2$ wherein M is an alkali metal cation, W is selected from aluminum, gallium, and mixtures thereof, Y is selected from silicon, germanium and mixtures thereof, and R is an organic cation. SSZ-13 zeolites can have a $YO_2:W_2O_3$ mole ratio greater than about 5:1. As prepared, the silica:alumina mole ratio is typically in the range of 8:1 to about 50:1; higher mole ratios can be obtained by varying the relative ratios of reactants. Higher mole ratios can also be obtained by treating the zeolite with chelating agents or acids to extract aluminum from the zeolite lattice. The silica:alumina mole ratio can also be increased by using silicon and carbon halides and similar compounds. Preferably, SSZ-13 is an aluminosilicate wherein W is aluminum and Y is silicon.

Uncalcined SSZ-13 zeolites, as prepared (with the organic templating component present in the crystal structure), have a crystalline structure whose X-ray powder diffraction pattern shows the characteristic lines shown in Table 1 below:

TABLE 1

| 2 θ | d (A) | 100 I/I$_0$ |
| --- | --- | --- |
| 9.57 | 9.24 | 61 |
| 14.06 | 6.30 | 21 |
| 16.23 | 5.46 | 80 |
| 17.82 | 4.98 | 24 |
| 20.87 | 4.26 | 100 |
| 22.14 | 4.01 | 9 |
| 22.72 | 3.91 | 8 |
| 25.01 | 3.56 | 69 |
| 26.30 | 3.589 | 18 |
| 31.00 | 2.885 | 47 |
| 31.29 | 2.859 | 21 |

The X-ray diffraction pattern of SSZ-13 is completely indexed on a rhombohedral lattice. SSZ-13 has been found to possess the crystal structure of chabazite.

The rhombohedral unit cell of SSZ-13 shows significant change between the as-prepared condition (with the organic templating component present in the structure) and the condition after calcination. The rhombohedral lattice provides appreciable flexibility. With the organic templating species present in the crystal structure, the volume of the unit cell is 7 cubic Angstroms (one percent) larger than the volume of the unit cell after calcination. Calcined SSZ-13 zeolites have a crystal structure whose X-ray diffraction pattern shows the characteristic lines shown in Table 2 below:

TABLE 2

| 2θ | d/n | 100 I/I₀ |
|---|---|---|
| 9.62 | 9.19 | 100 |
| 13.04 | 6.79 | 32 |
| 16.22 | 5.46 | 18 |
| 18.00 | 4.93 | 16 |
| 20.87 | 4.26 | 50 |
| 23.36 | 3.808 | 6 |
| 25.23 | 3.530 | 18 |
| 26.26 | 3.394 | 11 |
| 31.02 | 2.883 | 27 |
| 31.44 | 2.846 | 13 |

The synthetic SSZ-13 zeolites can be used as synthesized or can be thermally treated (calcined). Usually, it is desirable to remove the akali metal cation by ion exchange and replace it with hydrogen, ammonium, or any desired metal ion. The zeolite can be leached with chelating agents, e.g., EDTA, or dilute acid solutions to increase the silica:alumina mole ratio. The zeolite can also be steamed; steaming stabilizes the crystalline lattice to attack from acids.

The hydrogen, ammonium, and metal components can be exchanged into the zeolite. The zeolite can also be impregnated with the metals, or, the metals can be physically intimately admixed with the zeolite using standard methods known to the art. And, the metals can be occluded in the crystal lattice by having the desired metals present as ions in the reaction mixture from which the SSZ-13 zeolite is prepared.

The SSZ-13 aluminosilicate can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols or gels including mixtures of silica and metal oxides. Use of an active material in conjunction with the synthetic zeolite, i.e., combined therewith, tends to improve the conversion and selectivity of the catalyst in certain organic conversion processes. Inactive materials can serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powder-like materials which cause problems in processing.

Naturally occurring clays which can be composited with the synthetic zeolites of this invention include the montmorillonite and kaolin families, which families include the sub-bentonites, and the kaolins, in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-13 zeolites can be composited with porous matrix materials and mixtures of matrix materials such as silica, alumina, titania, magnesia, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-13 zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

RESULTS

A sample of SSZ-13 was produced (by synthesis) with $SiO_2/Al_2O_3=42$. Deactivation by coking was much slower during $C_6$ cracking (Table 3). Methanol conversion data with the higher silicon catalyst is shown in Table 4. As coking is much slower, only about 10% (wt) alkanes are formed in this instance. Even though this material cokes more slowly than a lower ($<12$) $SiO_2/Al_2O_3$ catalyst, there is still room for catalyst improvement since deactivation was still substantial (approximately 80% over two hours).

In the examples given below, the experimental conditions for the preparation of SSZ-13 zeolite, their conversion to catalysts and their use with pure compound feeds are described.

EXAMPLE 1

Ninety (90) grams of Banco "N" silicate (38.3% solids, $Na_2O/SiO_2=1:3.22$), 108 grams $H_2O$ and 18 grams of N,N,N trimethyl-1-ammonium adamantane (described in our U.S. patent application Ser. No. 519,954) are combined to form a solution. A second solution containing 12.0 grams $Al_2(SO4)_3.18H_2O$ and 18.66 grams of NaOH in 108 ml $H_2O$ is prepared and mixed with the first solution. The resulting solution is loaded into the Teflon liner of a stainless steel reactor (Parr), the reactor closed, and the contents heated static for 144 hours at 140° C. The resulting product, after washing and filtering, had $SiO_2/Al_2O_3=10$ by chemical analysis. The X-ray diffraction pattern of this product is that of SSZ-13.

EXAMPLE 2

5.05 Grams of Ludox AS-30 (30% $SiO_2$), 6 ml $H_2O$ and 2.02 grams of the organic cation of Example 1 are combined. A second solution of 0.50 gram $Al_2(SO_4)_3 \cdot 18H_2O$ and 1.16 grams of 50% NaOH reagent in 6 ml $H_2O$ is prepared and added to the first solution to produce a gel. After loading into a Parr reactor, the contents are heated at 150° C. for 144 hours with tumbling at 30 rpm. After cooling the reactor, the contents are washed and filtered and dried. The product, an SSZ-13 zeolite, had $SiO_2/Al_2O_3=42$ by chemical analysis. This is the higher silicon sample referred to in the catalytic examples that follow. The X-ray diffraction pattern of this sample shows SSZ-13.

EXAMPLE 3

The SSZ-13 zeolite in Examples 1 and 2 were both calcined, ion-exchanged, and recalcined under the following procedure. A temperature increase in steps of 200° F., 400° F., 600° F., and 800° F. for two hours each was used for heating at 1000° F. for eight hours. A finishing step at 1100° F. for four hours removes the last of the organic material. The calcination was performed in an atmosphere of 50% air, 50% $N_2$. Ion-exchange is performed four times with an excess of $NH_4/NO_3$, each treatment being two hours at 95° C. in approximately 500 cc $H_2O$. The second calcination cycle of the exchanged zeolites was identical to the preceding cycle omitting the final heating at 1100° F. X-ray diffraction patterns demonstrate calcined SSZ-13.

EXAMPLE 4

Cracking of $C_6$ hydrocarbons by the catalysts prepared from Examples 1 and 2 was carried out as follows: A 50/50 (w/w) mixture of n-hexane and 3-methyl pentane was passed at a rate of 1 ml/hr over 1 gram of catalyst packed in a microreactor. Helium (20 ml/min., 1 atm.) was used as the carrier gas. Reaction temperature was 800° F. Results are shown in Table 3.

EXAMPLE 5

Methanol conversion using each SSZ-13 catalyst was carried out at SV g/g/hr about 2. Helium at 20 ml/min. was used as carrier gas, and the catalyst (1 gram) was packed in a microreactor and heated at 800° F. during reaction. The product distribution is shown in Table 4. The conversion of methanol to hydrocarbons dropped from 85% to 10% over two hours. The lower $SiO_2/Al_2O_3$ catalyst deactivated completely in less than an hour.

TABLE 3

| ($SiO_2/Al_2O_3 = 10$) | | ($SiO_2/Al_2O_3 = 42$) | |
|---|---|---|---|
| Time (Min.) | % n-$C_6$ Converted | Time (Min.) | % n-$C_6$ Converted |
| 20 | 32 | 20 | 27 |
| 46 | 17 | 43 | 25 |
| 89 | 9 | 87 | 20 |
| 207 | 6 | 162 | 14 |
| | | 295 | 14 |
| | | 325 | 13 |

TABLE 4

PRODUCT DISTRIBUTION FOR METHANOL CONVERSION FROM HIGH SILICA SSZ-13 ($SiO_2/Al_2O_3 = 42$)

| Product | Wt % |
|---|---|
| Methane | 4.7 |
| Ethene | 35.0 |
| Ethane | 4.7 |
| Propene | 29.0 |
| Propane | 1.2 |
| Butenes | 15.0 |
| Butanes | 0.4 |
| $C_5+$ | 5.9 |
| Aromatics | 0 |

Wt % $C_2$-$C_4$ Products - 88% (93% olefins)

What is claimed is:

1. The process of converting methanol to olefins comprising contacting a methanol feedstock with SSZ-13 zeolite having an $SiO_2/Al_2O_3$ ratio by weight greater than about 20 under methanol conversion conditions.

2. The process of claim 1 wherein the $SiO_2/Al_2O_3$ ratio by weight is greater than about 30.

3. The process of claim 1 wherein the $SiO_2/Al_2O_3$ ratio by weight is greater than about 40.

* * * * *